United States Patent [19]

Hildebrandt

[11] 4,088,028
[45] May 9, 1978

[54] METHOD AND APPARATUS FOR ADJUSTING DEFECT SIGNAL GATE IN ULTRASONIC TEST CIRCUIT

[75] Inventor: Heiner H. G. Hildebrandt, Bensberg-Refrath, Germany

[73] Assignee: Krautkramer-Branson, Incorporated, Stratford, Conn.

[21] Appl. No.: 776,000

[22] Filed: Mar. 9, 1977

[30] Foreign Application Priority Data

May 10, 1976 Germany .............................. 2620590

[51] Int. Cl.² .......................................... G01N 29/04
[52] U.S. Cl. ....................................... 73/611, 73/624
[58] Field of Search ............................... 73/67.7, 67.9

[56] References Cited
U.S. PATENT DOCUMENTS

| | | | |
|---|---|---|---|
| 3,646,805 | 3/1972 | Walters | 73/67.9 |
| 3,942,358 | 3/1976 | Pies | 73/67.7 |
| 3,986,389 | 10/1976 | Mesina et al. | 73/67.9 |

Primary Examiner—Charles A. Ruehl
Attorney, Agent, or Firm—Ervin B. Steinberg; Philip J. Feig

[57] ABSTRACT

In an ultrasonic pulse-echo test circuit a probe means is coupled via a liquid filled coupling path to a workpiece which undergoes motion relative to the probe means. For each search signal transmitted by the probe means the transit time of such signal is measured from the time of transmission by the probe means to the receipt of the workpiece rear surface responsive echo signal. A computer coupled to receive the transit time values is programmed to classify transit time changes as fast occurring changes, caused by changes in coupling path length, or as slow occurring changes, caused by workpiece thickness changes. A defect gate forming a part of the test circuit is controlled by adjusting its opening responsive to a change in coupling path length and its closing responsive to a workpiece thickness change.

13 Claims, 5 Drawing Figures

METHOD AND APPARATUS FOR ADJUSTING DEFECT SIGNAL GATE IN ULTRASONIC TEST CIRCUIT

BRIEF SUMMARY OF THE INVENTION

This invention refers to pulse-echo ultrasonic testing and particularly to an arrangement for adjusting signal gates during automatic thickness gaging or defect testing.

More specifically, this invention concerns the setting of gates in an ultrasonic test circuit for optimum conditions during automatic thickness gaging and during nondestructive testing of workpieces by determining changes in the acoustic coupling delay path between the probe and workpiece as well as in the workpiece thickness, such changes exhibiting a different time response which is evident during relative motion between the workpiece and the test probes.

Quite specifically, this invention concerns a measuring method for workpieces undergoing a translating motion wherein changes as described above are not only recognized but are also distinguished. The invention utilizes the pulse-echo test method with one or more transmit-receive probes disposed across the width of the workpiece surface. The transit time changes of the ultrasonic signal in the direction of the motion of the workpiece responsive to differences in the workpiece thickness and of the coupling medium path manifest themselves as motion dependent and, hence, differ with respect to time. The coupling path length as understood herein is the thickness of the liquid medium which provides the acoustic coupling path between the exit surface of the test probe, i.e., the end of its predetermined delay path, and the workpiece entrant surface.

In order to minimize the non-tested regions near the workpiece entrant and rear surfaces, continuous controlling of the defect gate during the test process is known and necessary, see for instance U.S. Pat. No. 3,942,358 issued to W. Pies. In prior art ultrasonic test processes the acoustic coupling path distance between the probe end and the workpiece surface and the pretravel distance within the test probe itself are assumed to be constant for the test probes used both during calibration and testing. This is accomplished by entering, for instance, for each probe in suitable storage means the values of the internal, fixed delay path and of the coupling path length determined during calibration and then recalling cyclically during testing when several probes are operated the value associated with each probe. The values are treated as constant correction factors for determining material thickness and for controlling the defect gate setting.

When using the common gap coupling method the transmit-receive test probes usually are coupled to the workpiece via a gap of several one-tenth millimeter, the gap being filled with a stream of flowing water or water under pressure. In view of the acoustic velocity difference between the coupling medium (e.g. water) and the workpiece (e.g. steel), changes in gap distance appear as measuring errors. For example, the acoustic velocity of water is only one-quarter of that of steel, resulting that the coupling gap with respect to transit time affects the measurement by a factor of four. Changes of the coupling gap are encountered during continuous testing as a result of deviations from a flat surface, undulations, cyclic motion of the moving workpiece or workpiece motion upon the transport roller mechanism. Similarly, motion of the probe support causes a momentary movement of the test probes relative to the workpiece entrant surface.

It is known further to test plate stock, strips or large diameter tubes with oscillating or rotating test probes in order to maximize the tested area. Particularly during the motion reversal phase, the test probes with their support frequently undergo on account of their inertia a momentary motion such that an increase of the coupling gap manifests itself as an apparent shift in position of the workpiece rear wall. This apparent shift causes the measured workpiece thickness to be too large by generally a factor of four which in turn, causes the existence of a non-tested workpiece region adjacent the rear wall since this region will be outside the open gate condition.

By virtue of the mechanical construction of the test probe support, the adjusted minimum gap distance between the probe and the workpiece surface normally cannot be reduced further, this gap distance being given by shoes or rollers (wear excluded). Hence, motion related movement of the probes together with their support will occur only in a direction as to cause a momentary increase of the gap distance.

A principal object of this invention, therefore, is the provision of an arrangement which in a simple and reliable manner distinguishes between brief coupling path changes and the more slowly occurring workpiece thickness changes. Resulting from this distinction the invention provides means for producing a more precise, fully automatic workpiece thickness indication and transit time values suitable for defect gate adjustments. The adjustments make it possible to detect and register defects disposed in regions adjacent the workpiece surface. In this manner the existence of a non-tested workpiece region near its rear surface is avoided.

The problem stated above is solved by separating the values pertaining to the gradually changing workpiece thickness from those pertaining to the relatively momentary coupling gap changes with the help of a computer utilizing trend analysis, that is, a comparison of the pulse transit times of the sequentially transmitted search signals. This is accomplished by forming in a suitably programmed computer the time related differential quotients of the difference between the pulse transit times of two consecutive search pulses having a known time interval and utilizing the computer program for classifying the changes as relatively fast or relatively slow occurring changes. This classification is simple since the time related differential quotients pertaining to material thickness changes differ from those pertaining to coupling path changes by a factor of ten. It is advantageous to use flexible programmable computers since results obtained empirically, which are specific to the particular problem, are readily taken into consideration.

The present invention, therefore provides an arrangement for determining the changes in acoustic coupling path length occurring during continuous and automatic ultrasonic testing and, hence, provides for a more accurate measurement of workpiece thickness. The presence of a defect in the workpiece does not affect the measurement since the defect is manifest as a sudden change and clearly distinguishable over an abnormal thickness change within the time domain.

One of the principal objects of this invention is, therefore, the provision of a new and improved ultrasonic pulse-echo test apparatus.

Another important object of this invention is the provision of means for more accurately controlling the setting of defect gates in an ultrasonic test apparatus testing flat workpieces, such as plate stock, undergoing translating motion relative to a test station.

Another object of this invention is the provision of an electronic circuit for an ultrasonic pulse echo test apparatus which distinguishes between differences of the ultrasonic signal transit time arising from changes in the acoustic coupling path and those arising from changes in workpiece thickness.

A further object of this invention is the provision of means for steadily controlling the setting of an echo signal gate in an ultrasonic test apparatus, such setting being responsive to changes in the acoustic coupling path between the test probe and the workpiece surface and changes in the workpiece thickness.

A still further object of this invention is the provision of a computer in an ultrasonic test apparatus for distinguishing between differences of the ultrasonic signal transit time arising from changes in the acoustic coupling path and those arising from changes in workpiece thickness, and the provision of means for controlling a defect gate responsive to such determination.

Further and still other objects of this invention will be more clearly apparent from the following description when read in conjunction with the accompanying drawings.

DETAILED DESCRIPTION OF THE INVENTION

Figure 1:
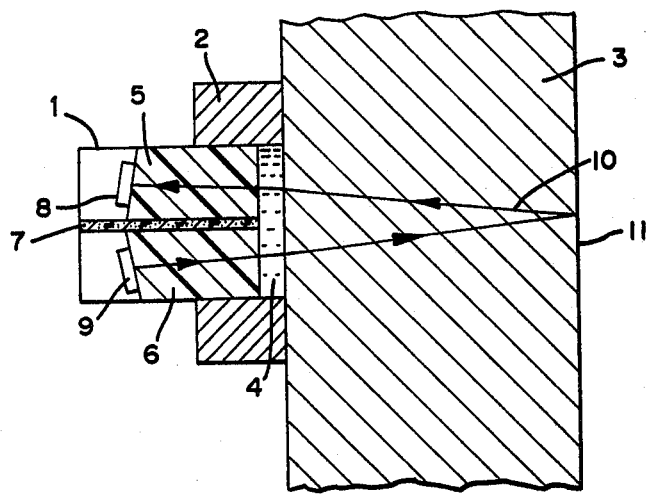
FIG. 1 is a sectional view of a typical transmit-receive test probe coupled to a workpiece.
Figure 2:
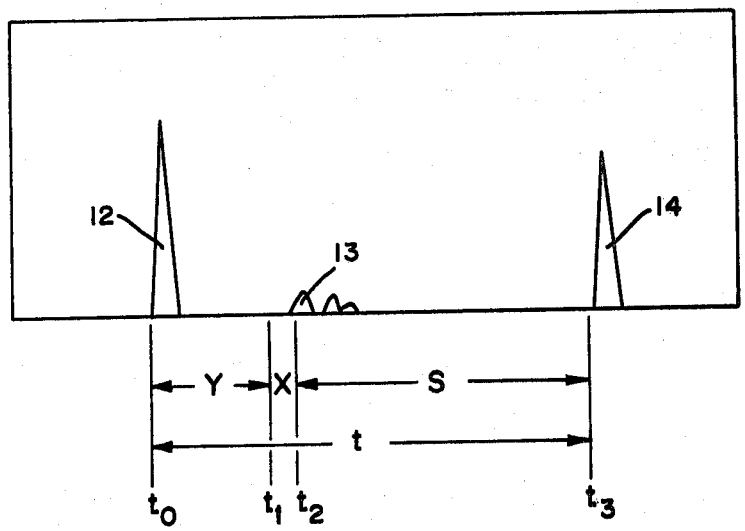
FIG. 2 is a representation of signals apparent on a cathode ray tube screen when testing a workpiece without a defect.
Figure 3:
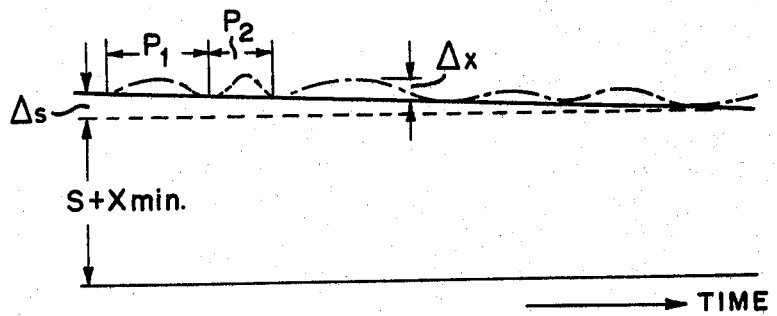
FIG. 3 is a graphic representation of the undulations experienced with a continuously moving workpiece, causing a non-periodic change of the coupling gap distance between the workpiece and the test probe.
Figure 4:
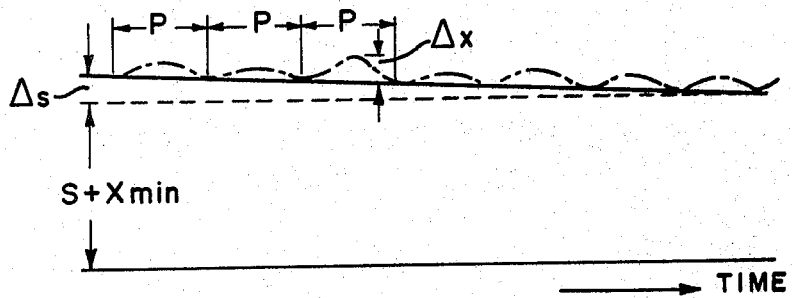
FIG. 4 is a graphic representation as shown in FIG. 3, however the change of the gap distance is periodic.

With reference to FIG. 1, a transmit-receive test probe 1 is disposed in a mechanical probe support 2 and is in acoustic energy transfer contact with a workpiece 3 via a water filled coupling distance or path 4. Ultrasonic search pulses transmitted cyclically from the transmit probe, for instance, a piezoelectric transducer element 9, traverse a fixed delay distance 6 inside the probe, the water filled gap 4 and then enter the workpiece 3. Upon reaching the rear surface 11 of the workpiece, the seach pulses are reflected and reflected energy travels in reverse direction across the gap 4, the delay distance 5 and reaches the receive transducer probe 8. The travel path 10 of the ultrasonic signals is indicated by the respective arrows. An acoustic barrier layer 7 inhibits cross coupling of acoustic signals between the transmit and receive portions of the probe. A cathode ray tube screen of an ultrasonic pulse-echo receiver shows an echo representation substantially as shown in FIG. 2, generally the transmit pulse signal 12 is not visible. Low amplitude acoustic interface echo signals 13 may be produced at the workpiece entrant surface by virtue of multiple reflections. The echo signal 14 arising from acoustic energy reflection at the workpiece surface 11 is indicated also in FIG. 2. The distance Y corresponds when related to transit time to the sum of the interval of fixed delay distances 5 and 6 which distances in the interval between two succeeding calibration procedures are considered to be constant since a constant related to the test probe itself is involved. The distance X corresponds to the water gap 4 (coupling path distance). This value generally is a minimum and is determined during calibration. During the test operation when the workpiece moves, this gap distance can only become greater on account of the motion of the test probe support. Mechanical wear is not pertinent to the present case. In accordance with the present invention and referring to FIGS. 3 and 4, the relatively fast occurring changes of the value X are identified as $\Delta x$ and the gradually more slowly occurring changes of the workpiece thickness S are identified as $\Delta s$. These illustrations refer always to one test probe track although it should be kept in mind that most commonly a workpiece is tested along a plurality of parallel tracks.

The coupling gap increase $\Delta x$, therefore, reflects itself as a transit time increase comprising the sum of the workpiece thickness S plus or minus $\Delta s$ and coupling path X. The transit time measured is then:

$$T = \left(\frac{Y}{V_y} + \frac{S \pm \Delta s}{V_p} + \frac{X + \Delta x}{V_k}\right) \cdot 2 \qquad \text{eq. 1}$$

The multiplication factor two is necessary since round trip time is measured. As used $V_y$ is the sound velocity of the fixed delay path in the probe, $V_k$ the sound velocity of the coupling gap, and $V_p$ the sound velocity of the workpiece.

The value of $\Delta x$ can only assume positive values since wear at the test probe and probe support are not considered. This value, however, can vary in an aperiodic manner, see $P_1$ and $P_2$ in FIG. 3, or in a periodic manner as seen at P FIG. 4.

Figure 5:
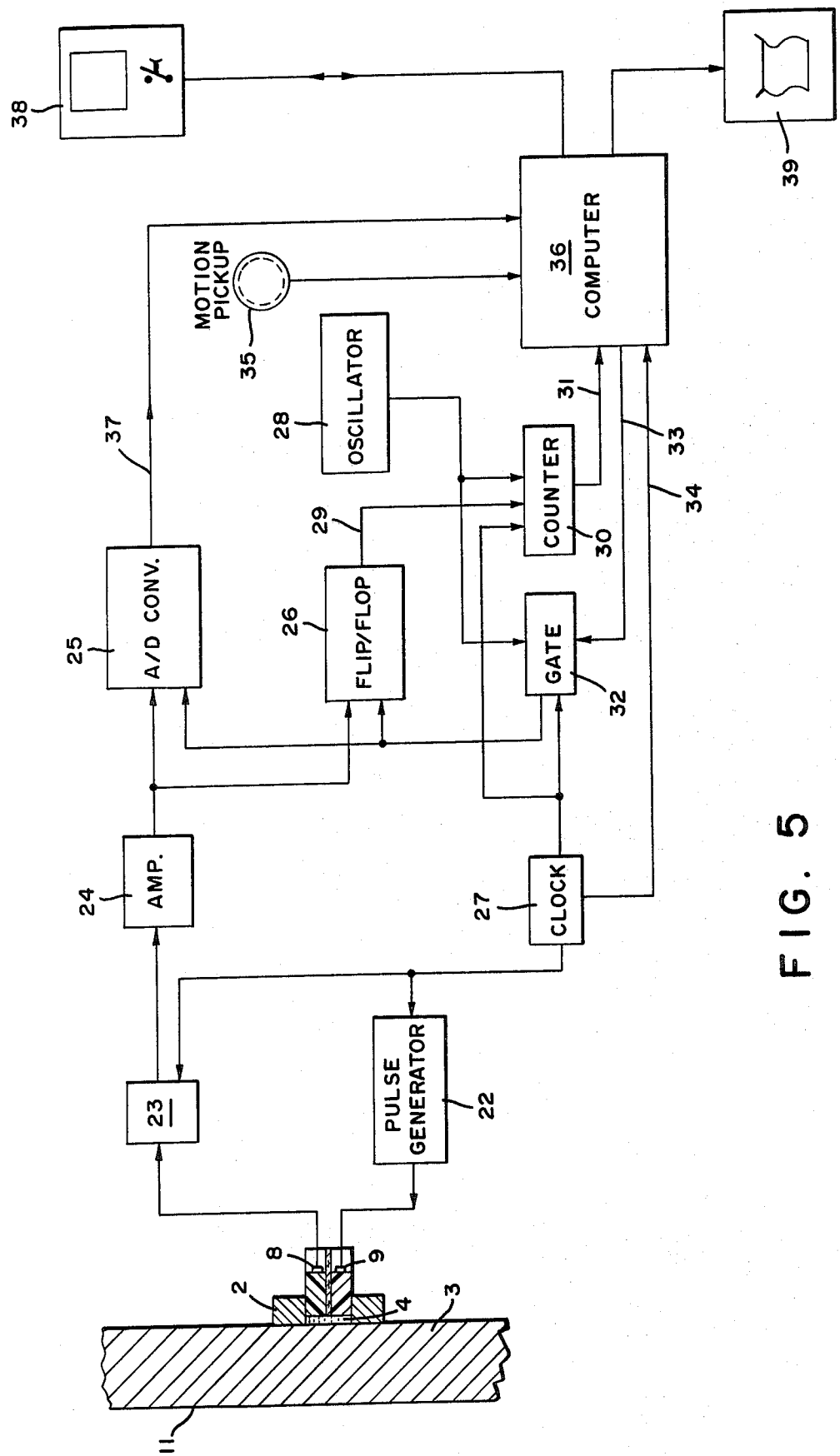
FIG. 5 is a schematic electrical circuit block diagram of a preferred embodiment of the invention.

Referring now to FIG. 5, the transmit-receive probe 1 is disposed in a support 2 and is coupled for acoustic energy transfer via a coupling path 4 to a workpiece 3. The transmit transducer 9 is coupled to a high frequency pulse generator 22 and is cyclically triggered by a clock 27. The receive transducer 8 converts the received ultrasonic echo signals from reflections along the test path to electrical signals which are coupled to a preamplifier 23. The preamplifier 23 is rendered operative by the clock 27 during the same cycle as the pulse generator 22. The amplified electrical signals from the preamplifier 23 are coupled to a main amplifier 24 which can have a linear or logarithmic gain characteristic. The amplified signals from the amplifier 24 are fed to an analog-to-digital converter 25 for amplitude evaluation and processing. If desired, the signals can be processed further also by known analog methods. The standardized and processed signals are provided via conductor 37 to the input of a suitable digital computer 36, such as is sold by Digital Equipment Corporation, computer Model PDP-11/35 with interface stage. The particular computer type is not significant for the present invention which concerns itself with the coupling path distance change.

For calculating the coupling path distance and changes thereof the entire transit time $t$ per test cycle must be determined. The clock 27 signals the start $t_0$ of the search pulse signal to the gate 32 serving as measuring gate, and to the counter 30 determining the transit time. The counter 30 when rendered operative by the clock 27 is triggered by an oscillator 28 for counting with highest accuracy even the smallest distances, e.g. 16 nanoseconds corresponding to 0.1 mm distance in steel. The counter 30 once started accumulates counts and is stopped upon the receipt of a rear wall 11 responsive echo signal along conductor 29. Hence, the count accumulated in the counter 30 corresponds to the total transit time $t$.

The adjustment of the defect gate 32, i.e., the gate interval, is made in response to the transit time value provided along conductor 33 from storage means or the computer 36, such transit time encompassing the fixed travel distance Y in front of the workpiece thickness S as well as the predetermined allowable or possible tolerance limits for "echo signal expected time interval". Within this interval, corresponding to the echo measurement gate, the gate 32 renders the A/D converter 25 as well as the stage 26 operable. The stage 26, for instance a flip-flop, serves for transit time end determination, that is, it fixes the time $t_3$ (rear wall echo responsive signal) the occurrence of which stops operation of the counter 30. It is known to determine this time also by other circuit means, such as amplitude comparators, slope discriminators, average value determination above base width, etc. The specific circuit used is not pertinent to the present invention.

The computer 36 receives the following signals and information:
(a) Pulse signals proportional to workpiece motion produced by a motion pickup means 35;
(b) Signals along conductor 31 responsive to the value of the transit time $t$;
(c) Clock signals along conductor 34 from the clock 27;
(d) From an input/output device 38 manually determined data during the calibration procedure relating to the permissible tolerance limits of the workpiece thickness $\Delta s$, the coupling path length changes $\Delta x$, data applicable to the theoretical or empirically derived magnitudes of typical rate changes and their limits per unit of time and unit of workpiece motion of $\Delta x$ and $\Delta s$;
(e) Further inputs for signal evaluation and processing of significant limits and parameters which however are not of significance for the coupling path distance problem.

The output from the computer 36 relating to data involving the evaluation of the test results is applied to suitable peripheral equipment 39, such as a printout device. Additionally, the input/output device 38 includes an alpha-numeric display unit. The input signals and data fed to the computer 36 or to an equivalent device are processed as follows:

For each cycle the transit time $t$ measured is stored and compared with the preceding value of $t$. The difference $\Delta t$ between both transit times is stored also. Referring to equation 1 above, since Y is a constant value, it follows:

$$\Delta t = \left( \frac{\Delta s}{V_p} + \frac{\Delta x}{V_k} \right) \cdot 2 \qquad \text{eq. 2}$$

The difference between both transit times $\Delta t$, therefore, is formed by the change in workpiece thickness $\Delta s$ and a change of coupling distance path $\Delta x$ taking into account the respective acoustic velocities. The differential quotient $\Delta s/\Delta t$, the workpiece thickness change derived over several test cycles, is significantly smaller than the differential quotient $\Delta x/\Delta t$, the change in coupling distance over the same quantity of test cycles. Hence, $\Delta s/\Delta t << \Delta x/\Delta t$. A computer, therefore, is capable of separating the slowly occurring changes $\Delta s$ from the faster occurring changes $\Delta x$. The relatively slow changes are identified as changes in workpiece thickness, and the faster changes as coupling path distance changes.

The change of total transit time, therefore, directly determines the closing (end) position of the defect gate for providing that no significant workpiece region adjoining the workpiece rear surface remains untested. When the result from the computer indicates that a fast transit time change occurs (change in coupling path length), the opening of the defect gate 32 is corrected accordingly by a signal along conductor 33. When the computer indicates that a slow transit time change occurs (workpiece thickness), the opening of the defect gate remains unchanged, but the closing of the gate 32 is adjusted correspondingly. In this manner, the defect gate, in all instances, remains the correct value for the prevailing workpiece thickness.

EXAMPLE

A test probe is coupled to a metal sheet 20 mm thick via a water coupling path distance of 0.5 mm average. The relatively high translational speed of the workpiece at 1 m/sec (corresponding to 1 mm/msec) due to surface undulations of the sheet material, typically 25 mm wave height peak-to-peak, per one meter of sheet length causes a change of the coupling path distance of 0.2 mm to 0.7 mm for a duration of 16 milliseconds. This increase in distance occurs despite the use of a spring force acting upon the probe support for causing probe engagement with the workpiece apex, yet inertia causes the probe support to be lifted momentarily as stated. The change in workpiece thickness resulting from production in the direction of the translating motion is assumed to be $\Delta s$ equal 0.1 mm per 100 mm workpiece motion. Since the acoustic velocity in steel is approximately four times greater than that in the water coupling medium, the coupling path change of 0.2 mm water distance corresponds to 0.8 mm distance related to steel. This change $\Delta x$ of 0.8 mm (value for steel) occurs in an interval of 16 milliseconds, which corresponds to a workpiece advance of 16 mm, i.e., $\Delta x = 0.1$ mm per 2 mm workpiece advance; at the same time the workpiece thickness changes at the rate of 0.1 mm per 100 mm workpiece advance with the result, assuming a clock frequency repetition frequency of 1 kHz from the clock means 27 (which corresponds to one search pulse per 1 mm workpiece advance), that the computer is capable of calculating the change of the transit time, that is the value of $\Delta t$ from cycle to cycle, which in the present instance is at an interval of 1 millisecond.

In view of the fact that in the stated example the change of 0.1 mm occurs per two test cycles corresponding to two millimeter of workpiece motion, this rapid change in transit time can be caused only by a change in the coupling path length. After the passing of the assumed 16 milliseconds the probe support once again will be completely in contact with the workpiece so that the minimum gap distance is restored. The computer is fully capable of performing a calculation within the cycle time of two times 16 milliseconds (i.e., within 32 milliseconds) corresponding to 32 mm workpiece advance for determining whether the variation is caused by a change in coupling distance or by a change in workpiece thickness.

If in the present example the changes in transit time were caused by a change in workpiece thickness, the change would be smaller by a factor of 50. The changes classified by the computer into two categories are used for defect gate correction. Such correction results in the defect gate being adjusted for the correct value of workpiece thickness and moreover, the defect gate open condition (gate width) being adjusted to reflect position changes of the rear wall responsive echo signal. In addition, the correct time related position of the workpiece entrant surface is provided to the computer. The latter information, for instance, is significant when utilizing time controlled gain for correcting the amplitude of a defect echo signal responsive to depth in the workpiece.

The limits of the changes of $\Delta t$, $\Delta x$ and $\Delta s$ possible per millimeter workpiece advance, or per test cycle respectively are dependent upon the specific test system and factors inherent in the manufacture of the workpiece. It is necessary, therefore, to estimate these variations in advance and enter the data in the computer program. In an alternative embodiment it is possible after calibration and during the early stage of the test procedure to derive the limits empirically, to test such data, and finally to enter the respective data in the program of the computer. In this latter case the use of a flexible programmable computer is most advantageous. Such a computer, more particularly, facilitates the adaption of the program to changes in operating conditions.

What is claimed is:

1. The method of testing by the ultrasonic pulse-echo method workpieces moving relative to a test probe means comprising:
   providing relative motion between a test probe means and a workpiece to be tested;
   periodically energizing said probe means for causing said probe means to transmit an ultrasonic search signal through a liquid coupling path into the surface of the workpiece and subsequently to receive at said probe means via said coupling path echo signals arising from an acoustic discontinuity encountered by the search signal along its path in the workpiece from the workpiece front surface to the workpiece rear surface and providing corresponding echo responsive electrical signals;
   transmitting the echo responsive electrical signals for evaluation to an electrical receiver circuit which includes a defect signal gate;
   measuring the transit time of the periodically transmitted search signal starting with the energization of said probe means and terminating with the receipt by said probe means of the workpiece rear surface responsive echo signal;
   determining whether a variation in transit time between successive search signals is caused by a change in the length of the coupling path or a change in workpiece thickness, and
   controlling said defect gate in response to such determination.

2. The method of testing as set forth in claim 1, said determining comprising measuring the transit time for each energization of said probe means, storing a value responsive to said transit time, comparing the stored value with the preceding value related to the preceding transit time, and storing the difference between both transit time values.

3. The method of testing as set forth in claim 1, said determining including forming time related differential quotients of the difference between two successive transit times.

4. The method of testing as set forth in claim 1, a change in coupling path length being manifest as a fast occurring variation in transit time between successive search signals and controlling the opening of said gate responsive to coupling path length changes, and a change in workpiece thickness being manifest as a slow occurring variation in transit time between successive search signals, and controlling the closing of said gate responsive to workpiece thickness changes.

5. The method of testing as set forth in claim 1, said controlling comprising setting the opening of said gate responsive to a predetermined change in coupling path length and setting the closing of said gate responsive to a change in workpiece thickness.

6. The method as set forth in claim 1, said measuring being accomplished by the use of a counter receiving counts during said transit time, and said determining being accomplished by the use of a digital computer which compares for each search signal a value associated with the respective transit time with a comparable value associated with the preceding transit times.

7. A pulse-echo ultrasonic test circuit comprising:
   electroacoustic probe means disposed for being coupled by means of a liquid filled coupling path to the entrant surface of a workpiece;
   electrical pulse generating means coupled to said probe means for periodically causing said probe means to be energized with an electrical pulse signal and said probe means to transmit in response to said pulse signal an ultrasonic search signal through said coupling path into a workpiece and subsequently to receive an echo signal arising from an acoustic discontinuity in the workpiece and to provide an electrical output signal responsive to such echo signal;
   receiving means including a defect signal gate coupled for receiving said output signal and processing such signal;
   means for providing relative motion between a workpiece and said probe means to cause sequentially different portions of such workpiece to be tested;
   means coupled to said probe means and to said receiving means for measuring the transit time of the periodically transmitted ultrasonic search signal from being generated by said probe means to the rear surface of the workpiece and providing a corresponding value, and
   computing means coupled to said means for measuring for receiving said value and determining whether a change in transit time between successively transmitted search signals is responsive to a thickness change of the workpiece or to a change in coupling path length and for controlling said receiving means responsive to such determination.

8. A pulse-echo ultrasonic test circuit as set forth in claim 7, said means measuring including a counter accumulating counts during each transit time.

9. A pulse echo ultrasonic test circuit as set forth in claim 8, said computing means comprising a cyclically operated digital computer.

10. A pulse-echo ultrasonic test circuit as set forth in claim 9, and means coupling said computing means to said gate for closing said gate in response to the receipt of a workpiece rear surface responsive echo signal and changing the opening of said gate in response to corresponding changes in coupling path length for causing the gate to be open for a time interval substantially coincident with the search signal traversing the workpiece thickness.

11. A pulse-echo ultrasonic test circuit comprising:
a clock providing periodic clock pulses;
electroacoustic probe means disposed for being coupled by means of a liquid filled coupling path to the entrant surface of a workpiece;
electrical pulse generating means coupled to said probe means and said clock for periodically causing said probe means responsive to a clock pulse to be energized with an electrical pulse signal and to transmit in response to said clock pulse an ultrasonic search signal through said coupling path into a workpiece and subsequently to receive an echo signal arising from an acoustic discontinuity in the workpiece intercepted by said search signal, said probe means providing an electrical output signal responsive to such echo signal;
receiving means including a defect signal gate coupled for receiving said output signal and processing such output signal;
means for providing translating motion between a workpiece and said probe means to cause sequentially a different portion of the workpiece to receive a respective search signal;
timing means coupled to said probe means for measuring for each search signal the transit time thereof, such time starting in response to the search signal being transmitted by said probe means and terminating in response to the receipt by said probe means of a respective workpiece rear surface echo responsive signal;
computing means coupled to said timing means, said clock, said means for motion and said receiving means for comparing for each energizing of said probe means the transit time of the respective search signal with the transit time of the preceding search signal and determining whether a change in transit time as related to workpiece translating motion is caused by a change in the length of the coupling path or a change in workpiece thickness and providing a corresponding control signal, and
means coupling said control signal to said gate for shifting the gate opening responsive to a change in coupling path length and shifting the gate closing responsive to a variation in workpiece thickness.

12. A pulse-echo ultrasonic test circuit as set forth in claim 11, said computing means comprising a digital computer and programmed for forming the time related differential quotients of the difference between the pulse transit times of every two consecutive search signals and programmed further for classifying the changes as relatively fast occurring changes related to coupling path length change or as relatively slow occurring changes related to worpiece thickness change.

13. A pulse-echo ultrasonic test circuit as set forth in claim 11, said timing means comprising a counter coupled to an oscillator for accumulating counts during the search signal transit time and the accumulated count being fed to said computing means.

* * * * *